United States Patent
Kitoh

(10) Patent No.: US 9,003,867 B2
(45) Date of Patent: Apr. 14, 2015

(54) GAS SENSOR, CONTACT MEMBER OF GAS SENSOR AND SENSOR ELEMENT RETAINING MEMBER FOR CONTACT MEMBER OF GAS SENSOR

(75) Inventor: Kenshin Kitoh, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 337 days.

(21) Appl. No.: 13/462,131

(22) Filed: May 2, 2012

(65) Prior Publication Data

US 2012/0216599 A1 Aug. 30, 2012

Related U.S. Application Data

(63) Continuation of application No. PCT/JP2010/067209, filed on Oct. 1, 2010.

(30) Foreign Application Priority Data

Nov. 9, 2009 (JP) .................................. 2009-256020

(51) Int. Cl.
*G01N 7/00* (2006.01)
*G01N 27/406* (2006.01)

(52) U.S. Cl.
CPC .................................. *G01N 27/4062* (2013.01)

(58) Field of Classification Search
CPC ............ G01N 27/407; G01N 27/4062; G01N 27/4078; Y10S 439/93; H01R 13/113; H01R 13/187; H01R 13/4223
USPC ................... 439/852; 73/31.05; 204/424, 426
See application file for complete search history.

(56) References Cited

U.S. PATENT DOCUMENTS

| 1,486,791 | A | * | 3/1924 | Nutt ............................... 439/862 |
| 3,363,224 | A | * | 1/1968 | Gluntz et al. .................. 439/852 |
| 3,815,081 | A | * | 6/1974 | Jones ............................. 439/747 |
| 3,818,424 | A | * | 6/1974 | Evans ............................ 439/852 |
| 4,556,475 | A | * | 12/1985 | Bayha et al. .................. 204/427 |
| 5,246,562 | A | * | 9/1993 | Weyl et al. .................... 204/424 |
| 5,573,650 | A | * | 11/1996 | Fukaya et al. ................ 204/424 |

(Continued)

FOREIGN PATENT DOCUMENTS

| JP | 2001-343356 A1 | 12/2001 |
| JP | 2002-168824 A1 | 6/2002 |

(Continued)

OTHER PUBLICATIONS

International Search Report dated Nov. 30, 2010.

*Primary Examiner* — Lisa Caputo
*Assistant Examiner* — Punam Roy
(74) *Attorney, Agent, or Firm* — Burr & Brown, PLLC

(57) ABSTRACT

To provide a gas sensor which can stably carry out a retention of a sensor element by a contact member and a reservation of an electric continuity between them. A contact member has an insertion port in which the sensor element is inserted and retained to obtain an electric connection with the sensor element. The contact member is provided with a plurality of sensor element retaining members which respectively have a plurality of abutting parts abutting on the sensor element, at least a part of a plurality of abutting parts is a first abutting part which has a leading end part formed as a linear shape or a point-like shape, and the leading end part of the first abutting part is a free end part which applies an elastic force to the sensor element while having point contact or line contact with the sensor element.

2 Claims, 9 Drawing Sheets

(56) References Cited

U.S. PATENT DOCUMENTS

| | | | |
|---|---|---|---|
| 5,890,936 A * | 4/1999 | McDonald et al. | 439/852 |
| 6,012,944 A * | 1/2000 | Hatakeyama | 439/441 |
| 6,672,136 B2 | 1/2004 | Kojima | |
| 7,340,942 B2 * | 3/2008 | Matsuo et al. | 73/31.05 |
| 7,918,695 B2 * | 4/2011 | Kutsuna | 439/845 |
| 7,931,502 B2 * | 4/2011 | Iida et al. | 439/630 |
| 8,287,294 B2 * | 10/2012 | Masuda et al. | 439/260 |
| 8,298,020 B1 * | 10/2012 | Chen | 439/852 |
| 8,641,438 B2 * | 2/2014 | Kamiya et al. | 439/260 |
| 2001/0025522 A1 | 10/2001 | Kojima | |
| 2004/0040370 A1 | 3/2004 | Kojima | |
| 2006/0243028 A1 * | 11/2006 | Nishio et al. | 73/31.05 |
| 2008/0099334 A1 * | 5/2008 | Yamauchi | 204/427 |
| 2009/0101503 A1 | 4/2009 | Kanao | |
| 2009/0291600 A1 * | 11/2009 | Kutsuna | 439/845 |
| 2012/0031171 A1 * | 2/2012 | Masuda et al. | 73/31.05 |
| 2012/0192653 A1 * | 8/2012 | Masuda et al. | 73/756 |

FOREIGN PATENT DOCUMENTS

| | | |
|---|---|---|
| JP | 2004-093306 A1 | 3/2004 |
| JP | 2006-284223 A1 | 10/2006 |
| JP | 2007-047075 A1 | 2/2007 |
| JP | 2009-115784 A1 | 5/2009 |

* cited by examiner

PRIOR ART

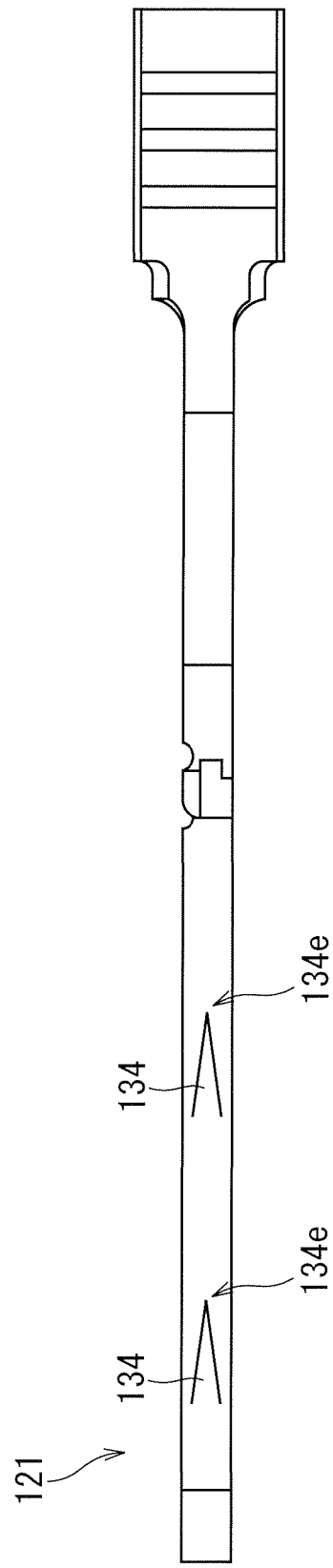

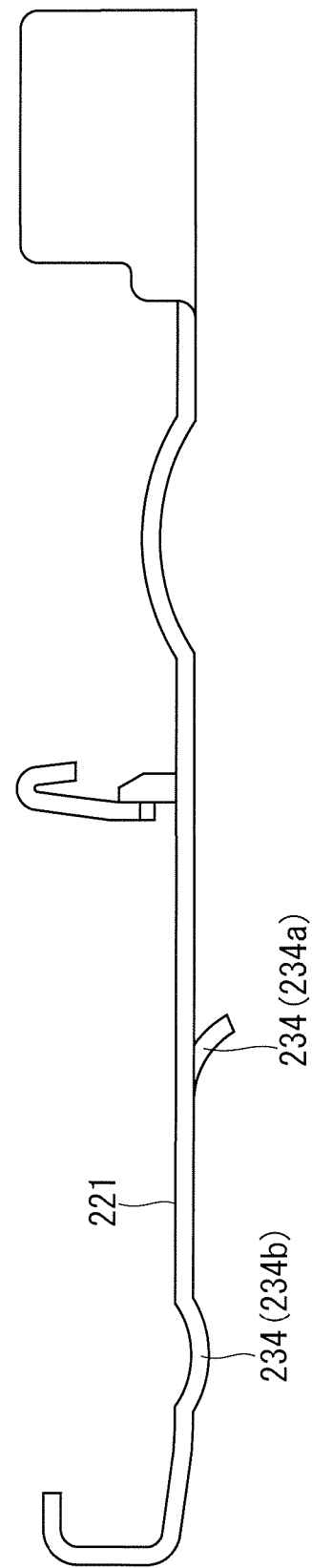

GAS SENSOR, CONTACT MEMBER OF GAS SENSOR AND SENSOR ELEMENT RETAINING MEMBER FOR CONTACT MEMBER OF GAS SENSOR

BACKGROUND OF THE INVENTION

1. Field of the Invention

The present invention relates to a gas sensor which measures a concentration of a predetermined gas component in a measurement gas by a sensor element, and more particularly to a technique of retaining and fixing the sensor element to a contact member.

2. Description of Related Art

Conventionally, in order to know a concentration of a desired gas component in a measurement gas, there have been employed various measuring apparatuses. For example, as an apparatus which measures an NOx concentration in the measurement gas such as a combustion gas or the like, there has been known a gas sensor (an NOx sensor) having a sensor element in which a Pt electrode and a Rh electrode are formed on a layer of a solid electrolyte having an oxygen ion conductivity such as a zirconia ($ZrO_2$) or the like (for example, see Japanese Patent Application Laid-Open No. 2006-284223 (Patent Document 1)).

The sensor element of the gas sensor mentioned above typically has a plurality of electrode terminals on a surface for applying an electric voltage, picking up a detection signal, supplying an electric power to a heater part and the like. Further, the gas sensor is provided with a contact member having a housing in which the sensor element is inserted and retained. The contact member is provided with a plurality of retaining members which are constructed by metal terminals, a plurality of lead wires which are connected to the retaining members and achieve an electric continuity between the sensor element and an external portion, and an insertion port in which the sensor element is inserted. In the gas sensor, the sensor element is inserted in the insertion port and the contact member retains the sensor element in such a manner that the retaining member comes into contact with the electrode terminal, so that the electric continuity between the sensor element and the external portion is obtained. For example, there has been already known a gas sensor in which a retaining member is provided with a plurality of convex parts as a contacting part between the sensor element and the electrode terminal, which are directed to the electrode terminal while a sensor element is inserted, and in which a retention of the sensor element and a reservation of a continuity are carried out by causing an elastic deformation in the convex part with an energization from an outer side (a fastening of a contact member) (for example, see Japanese Patent Application Laid-Open No. 2002-168824 (Patent Document 2)).

In the case of carrying out the retention of the sensor element and the reservation of the electric continuity in accordance with an aspect disclosed in Japanese Patent Application Laid-Open No. 2002-168824 (Patent Document 2), an elastic deformation of the convex part acting as a contact part with the electrode terminal due to the energization from the external portion is caused in such a manner that a contact area with the electrode terminal is increased in comparison with that in a non-contact time. In this case, there is such a problem that, since a surface pressure in the contact part is reduced in accordance with an increase in the contact area and a nonconductor film is formed in the contact part, a contact failure tends to occur. Further, there is such a problem that, since an elastic area (a limit of deforming by an elastic deformation) is small in the convex part in the first place, a plastic deformation tends to be caused. If the plastic deformation is caused, the surface pressure in the contact part becomes smaller in comparison with that in the elastic deforming time. After all, the contact failure tends to be caused.

SUMMARY OF THE INVENTION

The present invention is made by taking the problem mentioned above into consideration, and an object of the present invention is to provide a gas sensor which can stably carry out a retention of a sensor element by a contact member and a reservation of an electric continuity between the sensor element and the contact member.

In order to solve the above problems, a first aspect of the present invention provides a gas sensor including: a sensor element; and a contact member having an insertion port in which the sensor element is inserted and retained to obtain an electric connection with the sensor element, wherein the contact member is provided with a plurality of sensor element retaining members which respectively have a plurality of abutting parts abutting on the sensor element, at least a part of the plurality of abutting parts is a first abutting part which has a leading end part formed as a linear shape or a point-like shape, and the leading end part of the first abutting part is a free end part which applies an elastic force to the sensor element while having point contact or line contact with the sensor element.

A second aspect of the present invention provides the gas sensor according to the first aspect, wherein the sensor element retaining member has a conductivity, the first abutting part is a part of the plurality of abutting parts, and the sensor element retaining member and the sensor element are electrically conducted by setting the first abutting part to a contact point.

A third aspect of the present invention provides the gas sensor according to the fifth aspect, wherein the plurality of abutting parts are two abutting parts, and the first abutting part which is one of the two abutting parts is positioned in a back side of the insertion port than the second abutting part which is the other.

A fourth aspect of the present invention provides a contact member having an insertion port in which a sensor element for a gas sensor is inserted and retained to obtain an electric connection with the sensor element, wherein the contact member includes a plurality of sensor element retaining members which respectively have a plurality of abutting parts abutting on the sensor element, at least a part of the plurality of abutting parts is a first abutting part which has a leading end part formed as a linear shape or a point-like shape, and the leading end part of the first abutting part is a free end part which applies an elastic force to the sensor element while having point contact or line contact with the sensor element in a state that the sensor element is inserted and retained in the insertion port.

A fifth aspect of the present invention provides the contact member of the gas sensor according to the fourth aspect, wherein the sensor element retaining member has a conductivity, the first abutting part is a part of the plurality of abutting parts, and the first abutting part comes to a contact point which electrically conducts the sensor element retaining member and the sensor element in a state that the sensor element is inserted and retained in the insertion port.

A sixth aspect of the present invention provides the contact member of the gas sensor according to the fifth aspect, wherein the plurality of abutting parts are two abutting parts, and the first abutting part which is one of the two abutting parts is positioned in a back side of the insertion port than the second abutting part which is the other.

A seventh aspect of the present invention provides a sensor element retaining member used in a contact member having an insertion port in which a sensor element for a gas sensor is inserted and retained, wherein the sensor element retaining member includes a plurality of abutting parts which abut on the sensor element, at least a part of the plurality of abutting parts is a first abutting part which has a leading end part formed as a linear shape or a point-like shape, and the leading end part of the first abutting part is a free end part which applies an elastic force to the sensor element while having point contact or line contact with the sensor element in a state that the sensor element is inserted and retained in the insertion port.

In accordance with the first to seventh aspects of the present invention, it is possible to stably retain the sensor element by the contact member.

Particularly, in accordance with the second, third, fifth and sixth aspects of the present invention, it is possible to more stably obtain a continuity between the sensor element and the electrode terminal which is provided in the gas sensor.

BRIEF DESCRIPTION OF THE DRAWINGS

FIG. 7 is a top elevational view of a retaining member 121 in accordance with a second embodiment.

FIG. 8 is a side elevational view of a retaining member 221 in accordance with a third embodiment.

DETAILED DESCRIPTION OF THE INVENTION

Outline Structure of Gas Sensor

First of all, a description will be given of a gas sensor 100 which is in common in each of embodiments of the present invention in detail mentioned later.

Figure 1A:
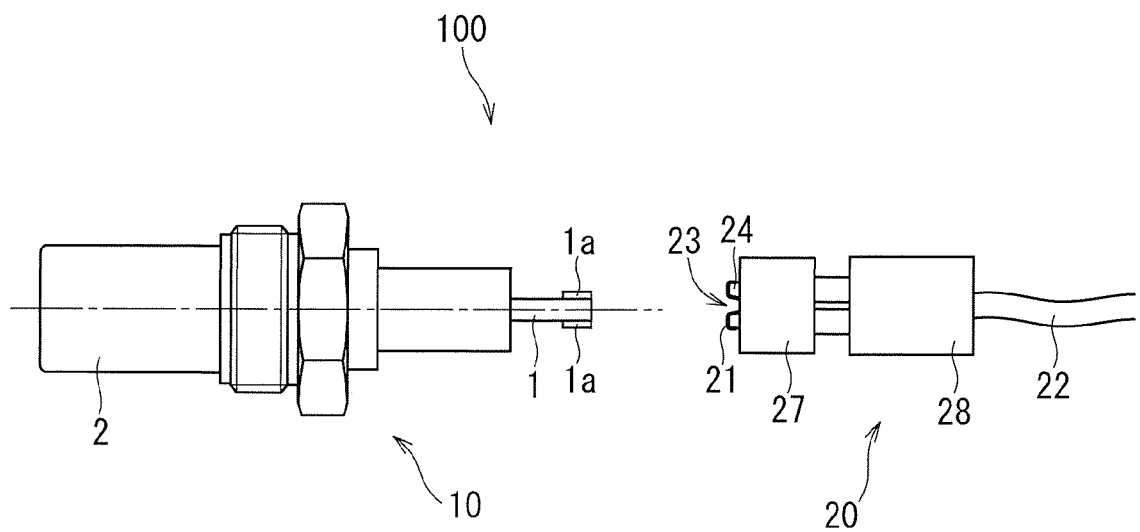
FIGS. 1A and 1B are views showing a situation at a time of assembling a gas sensor 100.
Figure 1B:
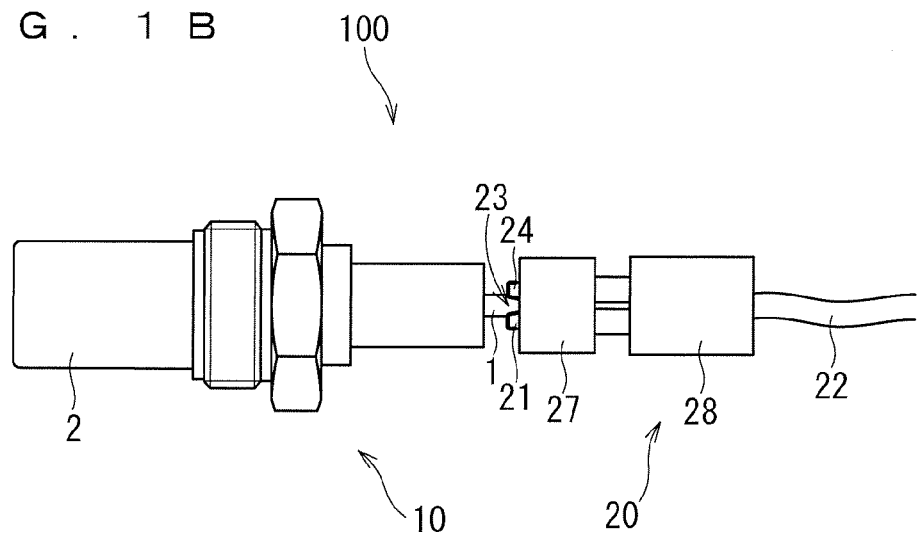

The gas sensor 100 is structured such as to detect a predetermined gas component (a target gas component) in a gas that is a measuring target (a measurement gas), and measure a concentration thereof. FIGS. 1A and 1B are views showing a situation at a time of assembling the gas sensor 100. FIG. 1A shows a situation before the assembling, and FIG. 1B shows a state after the assembling.

The gas sensor 100 has a structure in which a gas sensor main body 10 and a contact member 20 are integrated. The gas sensor main body 10 is provided with a sensor element 1 which is a gas detector, and an accommodating member 2 which accommodates the sensor element 1. On the other hand, the contact member 20 is mainly provided with a plurality of sensor element retaining members (hereinafter, refer simply to as a retaining member) 21, a lead wire 22 which is connected to the retaining members 21, and a housing 24 where the sensor element 1 is inserted and retained in an insertion port 23 via the retaining members 21.

As shown in FIG. 1B, the sensor element 1 provided in the gas sensor main body 10 is inserted in the insertion port 23 of the housing 24 provided in the contact member 20, and the sensor element 1 is retained in the housing 24 via the retaining member 21, whereby the gas sensor 100 is integrated. In the present embodiment, obtaining the gas sensor 100 by integrating the gas sensor main body 10 and the contact member 20 as mentioned above is called as "assembling the gas sensor 100", and a series of processing actions for achieving this is called as "an assembly of the gas sensor 100" or the like.

Figure 2:
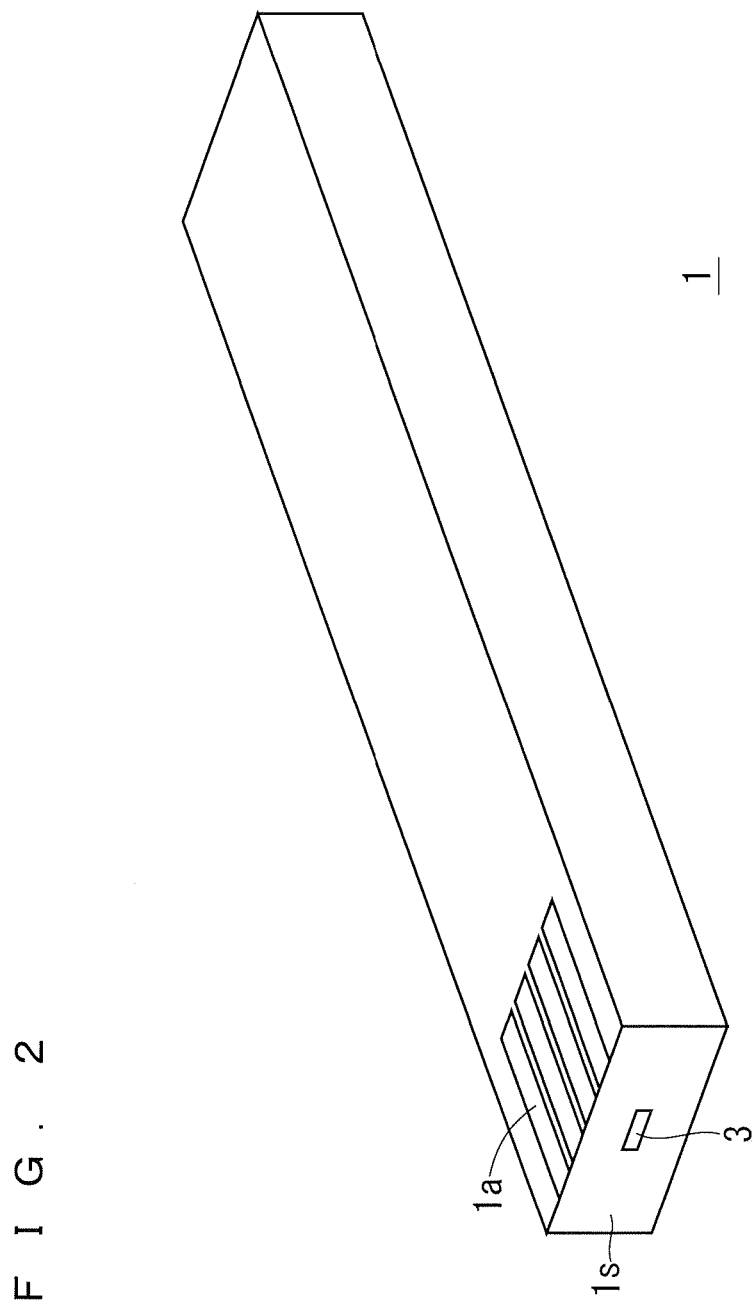
FIG. 2 is a perspective view showing an outer shape of a sensor element 1.

FIG. 2 is a perspective view showing an outer shape of the sensor element 1. The sensor element 1 has a structure in which a plurality of layers are laminated, each of which is constructed by an oxygen ion conducting solid electrolyte such as a zirconia ($ZrO_2$) or the like. Further, front and back surfaces of the sensor element 1 are provided with a plurality of electrode terminals 1a for applying an electric voltage, picking up a detected signal, supplying an electric power to a heater part and the like. In FIG. 2, there is illustrated the sensor element 1 in which four electrode terminals 1a are provided in one surface (an illustration of the electrode terminals 1a in the back surface side is omitted), however, this is just an exemplification, and the number of the electrode terminals 1a can be appropriately determined in accordance with the structure of the sensor element 1. Further, the sensor element 1 has a gas introduction port 3 introducing a reference gas in a leading end surface is in a side in which the electrode terminal 1a is provided, and is provided with a measurement gas introduction port which is not illustrated, in the other end portion.

The sensor element 1 is manufactured, for example, by carrying out following steps: performing a predetermined processing and printing an electrode and wiring pattern on ceramics green sheets each corresponding to each of the layers of the sensor element 1, thereafter laminating them and cutting in a predetermined magnitude, and burning the obtained laminated body. In the gas sensor 100, the target gas component is detected by utilizing a matter that an electric current corresponding to an abundance of the target gas component in the measurement gas flows between the predetermined electrodes provided inside at a time when the measurement gas is introduced to the sensor element 1.

Figure 3:
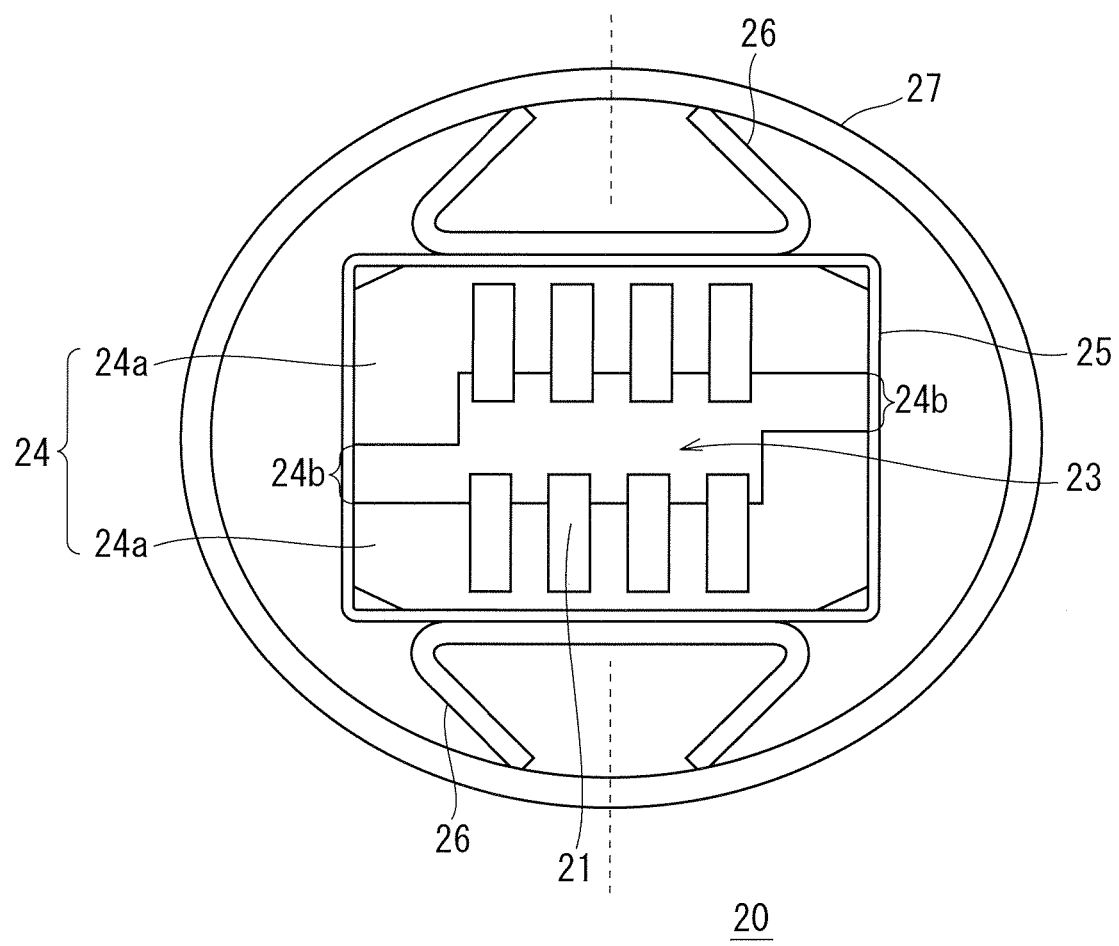
FIG. 3 is a view showing a contact member 20 as seen from a side of an insertion port 23.

FIG. 3 is a view showing the contact member 20 as seen from a side of the insertion port 23. As shown in FIG. 3, the housing 24 is constructed by a pair of housing members 24a which are arranged so as to be opposed to each other. These housing members 24a have approximately the same cross sectional shape, and are provided so as to be spaced from each other in order that a space having a rectangular shape in a cross sectional view serving as the insertion port 23 is formed between both the members. In other words, each of the housing members 24a can be said to have such a shape that a housing having a space inside and a rectangular shape in a cross sectional view is divided into two pieces. Further, each of the housing members 24a is structured such that when it receives an external force which heads for a vertical direction in the drawing view from inside of the insertion port 23, the vicinity of a leading end part thereof (the adjacence of an end part of the insertion port 23) deviates upward or downward within a certain range. In a state before the gas sensor 100 is assembled, gaps 24b are provided in end parts of two housing members 24a.

Further, the contact member 20 is provided with a fixing metal fixture 25 which is made of a metal material and is formed as a tubular shape, a pressing spring 26 which energizes the fixing metal fixture 25 toward the sensor element 1 at a time of fixing the sensor element 1, a caulking ring 27 which compressively deforms the pressing spring 26 with its outer periphery being caulked, and a grommet 28 (FIGS. 1A and 1B) which is formed in such a manner that the lead wire 22 is inserted inside thereof in an airtight manner. In this case, the fixing metal fixture 25 may be formed as a polygonal shape such as a quadrangular shape or the like, in addition to the tubular shape.

In a situation that the sensor element 1 is inserted in the insertion port 23 of the housing 24, when the caulking ring 27 is caulked and the pressing spring 26 deformed thereby energizes the fixing metal fixture 25, the fixing metal fixture 25 is compressively deformed in the vertical direction of FIG. 3. Thus, a distance of the insertion port 23 of the housing 24 is narrowed down, and thereafter, there is achieved a state that the retaining members 21 provided in the upper and lower housing members 24a respectively retain the sensor element 1 while energizing. In other words, it can be said that the state mentioned above is a state of pinching the sensor element 1 from two directions by plural pairs of retaining members 21 which are provided in two housing members 24a. In accordance with this, there can be achieved a state that the sensor element 1 is retained and fixed by the contact member 20. At that time, since the retaining member 21 comes into contact with the electrode terminal 1a, an electric continuity between the sensor element 1 and the external portion is achieved via the lead wire 22 which is connected to the retaining member 21.

First Embodiment

Subsequently, a description will be given sequentially of various embodiments of details of a structure of the retaining member which is a characteristic constructing element in the gas sensor in accordance with the present invention, an aspect of retaining the sensor element by the retaining member, and an aspect of a contact between the retaining member and the electrode terminal.

Figure 4:
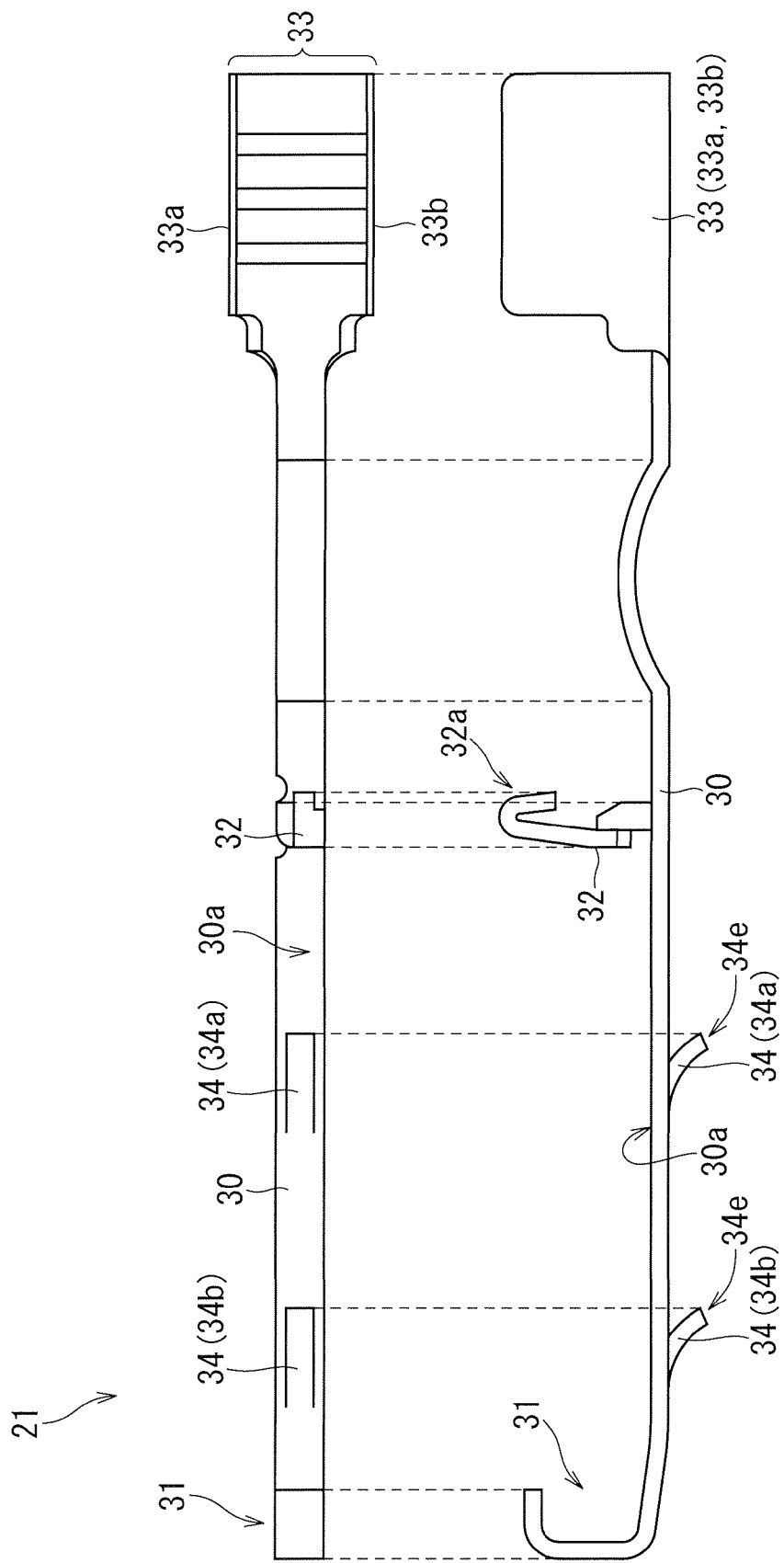
FIG. 4 is a view showing a top elevational view and a side elevational view of a retaining member 21 in accordance with a first embodiment in a parallelizing manner.
Figure 5:
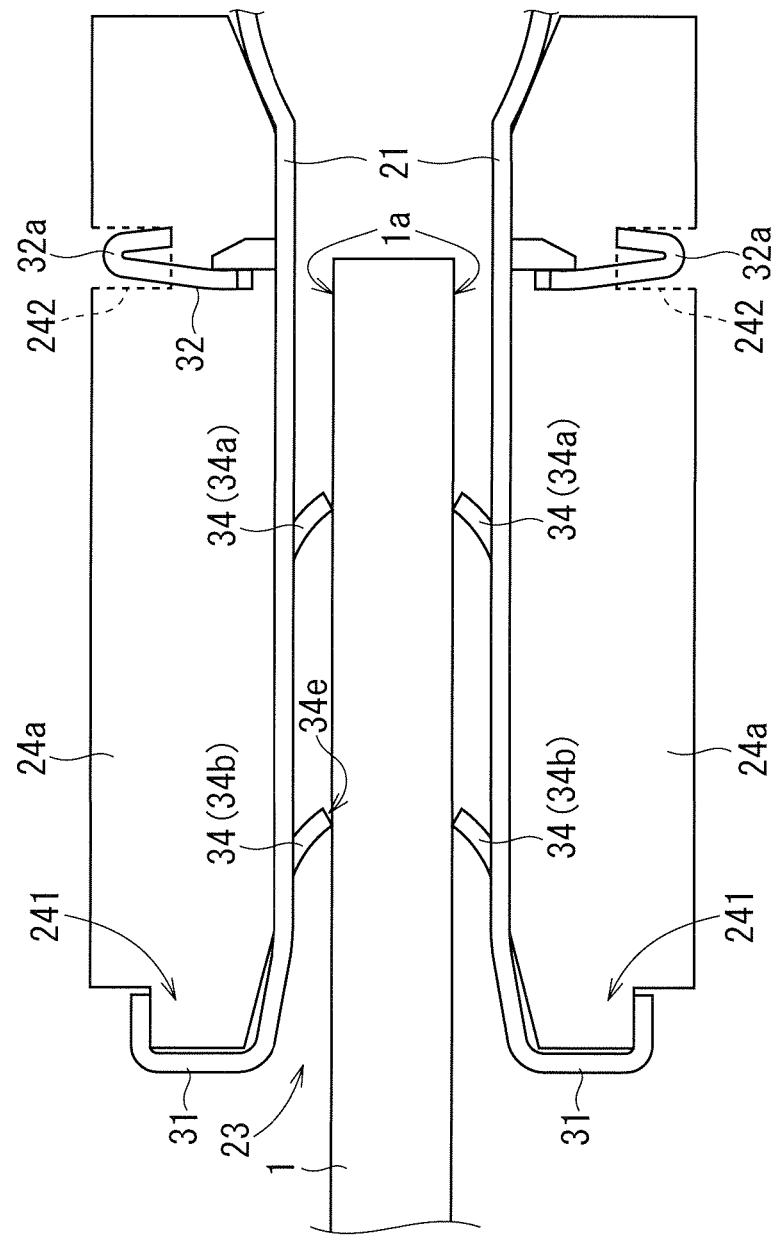
FIG. 5 is a partly side cross sectional view showing a state that a sensor element 1 is inserted in an insertion port 23 of a contact member 20 in which the retaining member 21 is embedded.

FIG. 4 is a view showing a top elevational view and a side elevational view of the retaining member 21 in accordance with the first embodiment in a parallelizing manner. FIG. 5 is a partly side cross sectional view showing a state that the sensor element 1 is inserted in the insertion port 23 of the contact member 20 in which the retaining member 21 is embedded. FIG. 5 shows a cross section which passes through a pair of upper and lower retaining members 21, however, the contact member 20 is actually provided with plural pairs of retaining members 21. For instance, FIG. 3 exemplarily shows the case that each of the upper and lower housing members 24a is provided with four retaining members, that is, four pairs of retaining members 21 are provided. The following description corresponds to all the retaining members 21.

The retaining member 21 has a first hooking part 31, a second hooking part 32, a crimping part 33, and an abutting part 34, along a base part 30 which extends in a right and left direction in the drawing view in FIG. 4 and FIG. 5 and is formed as an elongated laminar shape (may be called as a band shape). The retaining member 21 is produced by punching and bending a thin plate of a conductive metal. For example, it can be produced by a SUS to which a Ni plating is applied.

The first hooking part 31 and the second hooking part 32 both have a function of fixing the retaining member 21 to the housing member 24a at a time of assembling the contact member 20. The first hooking part 31 is a part which is provided in one end portion of the retaining member 21 (a left end portion in FIG. 4 and FIG. 5), and it is successive from the base part 30 and has an approximately C-shaped form in a side elevational view. On the other hand, the second hooking part 32 is a part which protrudes vertically (in a vertical direction in FIG. 4 and FIG. 5) from the base part 30, and it has a leading end part 32a folded as an approximately U-shaped form in a side elevational view.

When the contact member 20 is embedded, the first hooking part 31 is hooked to a first hooked part 241 which is provided in one end portion (a left end portion in FIG. 5) of the housing member 24a, as shown in FIG. 5. For realizing this, the shapes of the first hooking part 31 and the first hooked part 241 are defined in such a manner that the hooking state mentioned above can be well retained. In other words, the first hooking part 31 is processed in such a manner as to have a shape which is along a side cross sectional shape of the first hooked part 241. In this case, in the housing member 24a shown in FIG. 5, the first hooked part 241 is formed as a projection shape in a side cross sectional view; however, this is not an essential aspect. In place of this, it is possible to employ such an aspect that a whole of an end portion of the housing member 24a is formed as the first hooked part 241, and the first hooking part 31 is hooked to the end portion.

On the other hand, the second hooking part 32 is inserted from one surface side of the housing member 24a as shown in FIG. 5, and it is hooked to a second hooked part 242 which is a concave portion provided in an opposite surface side of the housing member 24a in a manner that the leading end part 32a energizes the second hooked part 242 with its elastic force.

As a result of hooking of the first hooking part 31 and the second hooking part 32 to the housing member 24a as mentioned above, the retaining member 21 is fixed to the housing member 24a in a manner that the abutting surface 30a of the base part 30 abuts on the housing member 24a.

The crimping part 33 is a part which is provided in an end portion (a right end portion in FIG. 5) opposite to the first hooking part 31 in the retaining member 21, and is provided for jointing the lead wire 22 to the retaining member 21. The crimping part 33 comprises a pair of crimping plates 33a and 33b each of which is a flat plate being respectively successive from the base part 30 and being vertical to the base part 30. When the contact member 20 is assembled, the end portion of the lead wire 22 inserted through the grommet 28 is interposed between the crimping plates 33a and 33b, and an external force is applied between the crimping plates 33a and 33b so as to crimp the crimping plates 33a and 33b to the lead wire 22. Thus, the lead wire 22 is fixed to the retaining member 21.

The abutting part 34 is a part which directly abuts on the sensor element 1 at a time when the sensor element 1 is retained to the contact member 20. Further, the abutting part 34 can serve as a contact point which obtains an electric continuity with respect to the electrode terminal 1a provided in the sensor element 1.

The abutting part 34 is provided with a cut portion having a rectangular shape in a top elevational view in a part of the base part 30, with its leading end part 34e protruding to an opposite side to the contact surface 30a. In other words, the abutting part 34 is provided as a cantilever beam shape in which the leading end part 34e comes to a free end portion. In addition, the abutting part 34 serves as a leaf spring which has a fixed end in a side of the base part 30, and applies a restoring force (an elastic force) to the sensor element 1 at a time when the sensor element 1 is fixed. In this case, referring for confirmation, the leading end part 34e is indicated by a point in FIG. 4 and FIG. 5; however, it is practically a linear position which extends in a direction being vertical to the drawing.

In the case shown in FIG. 4 and FIG. 5, two abutting parts 34 are provided in one retaining member 21. Hereinafter, the abutting part 34 in a far side (a back side of the insertion port 23) from the end portion of the insertion port 23 is called as a first abutting part 34a, and the abutting part 34 in a near side (a near side of the insertion port 23) from the end portion of the insertion port 23 is called as a second abutting part 34b. In the case mentioned above, it is a preferable example that a manner of forming the electrode terminal 1a in the sensor element 1 and a manner of arranging the abutting part 34 in the retaining member 21 are determined in order that at least the first abutting part 34a in two abutting parts 34 serves as a contact point which obtains an electric continuity with respect to the electrode terminal 1a of the sensor element 1, in addition to a role of retaining the sensor element 1. It is to be noted that it is possible to employ such an aspect that a larger number of abutting parts 34 are provided.

Figure 6A:
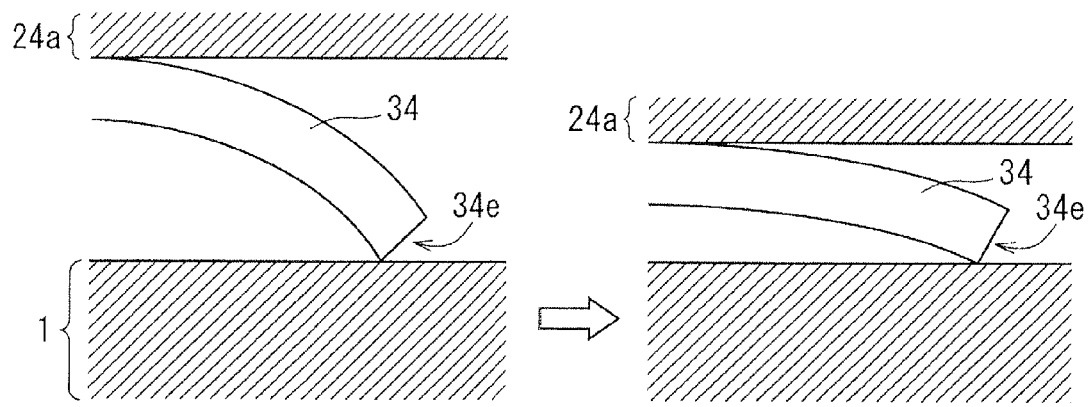
FIGS. 6A and 6B are side cross sectional views showing an appearance of a contact between a abutting part 34 and the sensor element 1 in the retaining member 21 in comparison with a case of a retaining member which is provided in a conventional gas sensor.
Figure 6B:
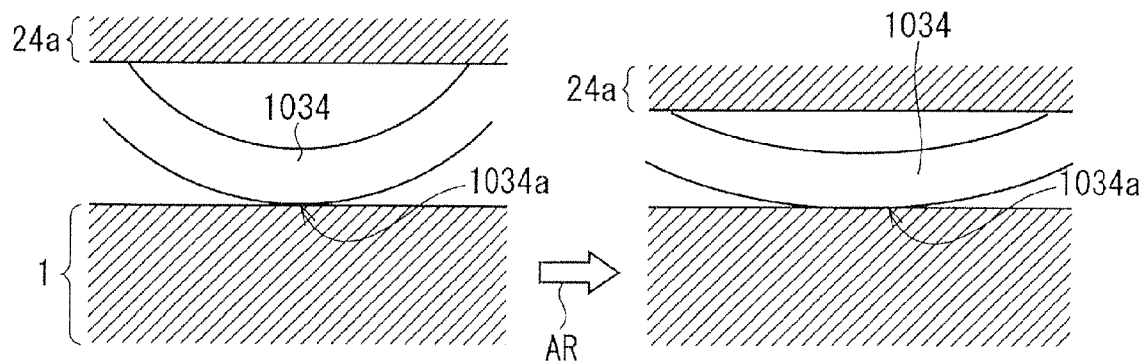

FIGS. 6A and 6B are side cross sectional views showing an appearance of a contact between the abutting part 34 and the sensor element 1 in the retaining member 21 with which the gas sensor 100 according to the present embodiment is provided, in comparison with the case of the retaining member with which the conventional gas sensor is provided. FIG. 6A shows the contact aspect in the present embodiment, and FIG. 6B shows the contact aspect in the case of using the conventional retaining member having a convex abutting part 1034. In both cases, a left side of an arrow AR in the drawing shows a state at a time of inserting the sensor element 1, and a right side thereof shows a state at a time of fixing the sensor element 1.

In the gas sensor 100 according to the present embodiment, after the sensor element 1 is inserted in the insertion port 23, the caulking ring 27 is caulked so that the sensor element 1 is fixed to the housing 24. More specifically, the sensor element 1 is retained and fixed with a balance of elastic forces (restoring forces of the leaf springs) which are applied from the abutting parts 34 of the retaining members 21 provided in the housing members 24a in both upper and lower sides. Further, as shown in FIG. 6A, until the sensor element 1 is retained and fixed after being inserted, only the leading end part 34e which is the free end portion abuts on the sensor element 1 in the abutting part 34. In other words, the leading end part 34e and the sensor element 1 keep an approximately linear contact state, while the sensor element 1 is inserted, and then retained and fixed. From another point of view, it can be said that the leading end part 34e corresponding to a free end portion of a cantilever beam displaces in accordance with the contact state with the sensor element 1.

On the other hand, in the case of the conventional gas sensor shown in FIG. 6B it is similar to the present embodiment in that the sensor element 1 is retained and fixed by being applied an elastic force from a abutting part 1034; however, even if the abutting part 1034 is in a linear contact state with the surface of the sensor element 1 in a vertex part 1034a at a time of inserting the sensor element 1, a contact area is expanded so as to be in a surface contact state at a time of the thereafter fixing.

Generally, a pressure (a surface pressure) acting on the contact region becomes larger as an area of the contact region is smaller. Thus, in the gas sensor 100 according to the present embodiment, it is possible to retain the sensor element 1 by a higher retaining force than the conventional one, even in the case that respective caulking rings 27 are caulked in the same manner.

Further, depending on a type of material for the electrode terminal 1a, there is a case that a nonconductor film which is a surface oxidation film of a metal constructing the electrode terminal 1a is formed in a contact portion with the retaining member of the electrode terminal 1a. In the case that the surface pressure in the contact portion is small such as the conventional structure, a displacement of the contact portion tends to be generated, and a nonconductor is newly formed in the portion each time when the contact portion changes. As a result, the contact failure tends to occur. On the contrary, in the case of using the retaining member 21 in accordance with the present embodiment, since the sensor element 1 is retained stably in the abutting part 34, the formation of the nonconductor mentioned above is suppressed. Accordingly, the use of the retaining member 21 in accordance with the present embodiment reduces the occurrence of the contact failure in comparison with the use of conventional one.

Further, in the case of the present embodiment, since the abutting part 34 deforms only toward the side of the base part 30, and the abutting part 34 becomes only in parallel to the base part 30 even if it deforms to the maximum, it always deforms within a range of an elastic area (a limit of deforming by an elastic deformation).

On the contrary, in the conventional case, though an illustration is simplified in FIG. 6B, there is a case that the abutting part 1034 may deforms plastically, depending on the degree of a force applied to the abutting part 1034 from a vertical direction. Once the plastic deformation is caused, the force retaining the sensor element 1 is weakened. As a result, the contact failure tends to occur.

Comparing the both, it is possible to more stably retain the sensor element 1 in the present embodiment than the conventional manner. Consequently, it is possible to more stably obtain a continuity with respect to the electrode terminal 1a.

As described above, in accordance with the present embodiment, it is possible to more stably retain the sensor element and it is possible to more stably obtain the continuity with the electrode terminal, by forming the abutting part of the retaining member in such a manner as to serve as the cantilever-beam-shaped leaf spring which abuts on the sensor element in the approximately linear contact state, and retaining the sensor element which is inserted in the insertion port by utilizing the restoring force of the leaf spring.

Second Embodiment

FIG. 7 is a top elevational view of a retaining member 121 in accordance with a second embodiment. In the retaining member 121 shown in FIG. 7, a cut portion formed as a triangular shape in a top elevational view of the abutting part 134 serves as the cantilever-beam-shaped leaf spring in the same manner as the abutting part 34 of the retaining member 21 in accordance with the first embodiment. In this case, in a state that the sensor element 1 is retained and fixed, a leading end part 134e which is a free end portion and the sensor element 1 keep an approximately point contact state. The retaining member 121 contacts with the sensor element 1 with a larger surface pressure than the retaining member 21 in accordance with the first embodiment. Accordingly, it is possible to retain the sensor element 1 by a higher retaining force than the first embodiment.

Third Embodiment

FIG. 8 is a side elevational view of a retaining member 221 in accordance with a third embodiment. Even in the retaining member 221 shown in FIG. 8, two abutting parts 234 (a first abutting part 234a and a second abutting part 234b) are provided in the same manner as the first embodiment; however, only the first abutting part 234a abutting on the electrode terminal 1a of the sensor element 1 has the same shape as the abutting part 34 in accordance with the first embodiment, and the second abutting part 234b is formed as a convex shape.

Even in the case of the retaining member 221 having the aspect mentioned above, it is possible to obtain the same operations and effects as the first embodiment, in the first abutting part 234a which serves as the contact point with the electrode terminal 1a. Accordingly, if the second abutting part 234b is formed in such a manner that it can apply a sufficient elastic force for retaining the sensor element 1, it is possible to obtain a sufficient retaining force and a reservation of a stable continuity even in the case of using the retaining member 221 in accordance with the present embodiment.

It is to be noted that, in the case that more than two abutting parts 234 are provided, the abutting parts 234 having the same shape as the first abutting parts 234a, and the abutting parts 234 having the same shape as the second abutting parts 234b may be provided at an appropriate number at appropriate positions.

<Variations>

Figure 9:
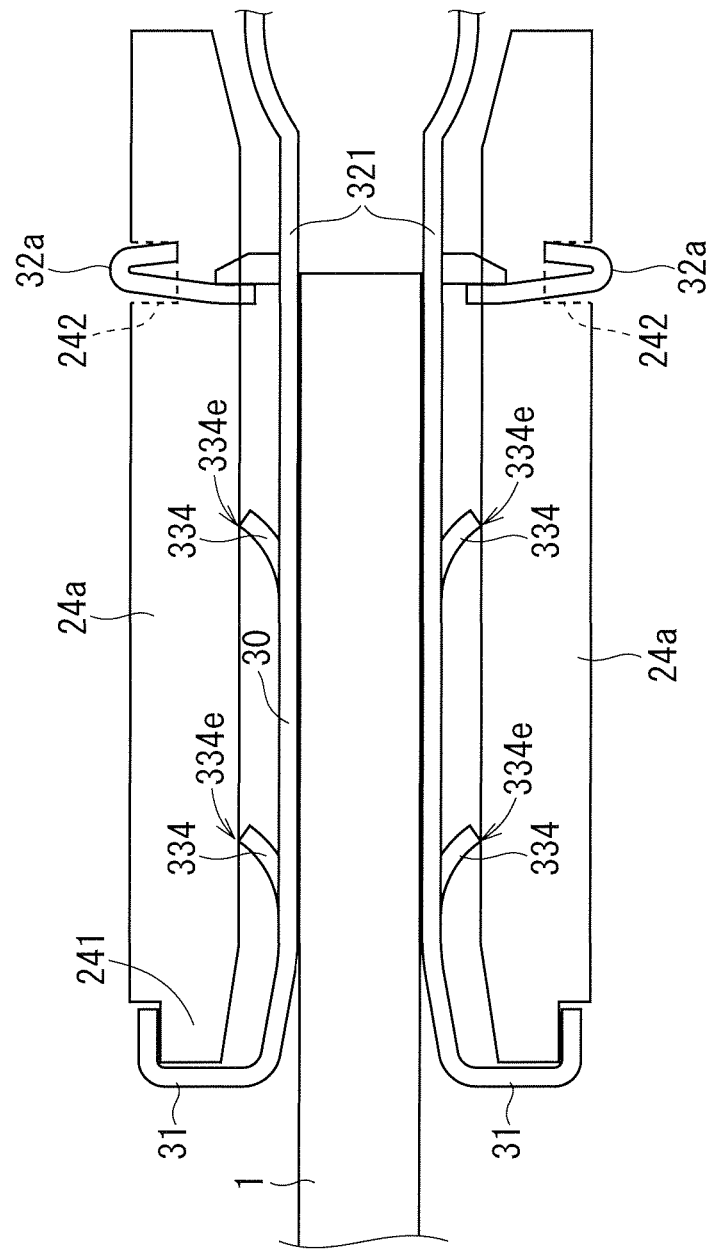
FIG. 9 is a side cross sectional view showing an appearance of a contact between a contact portion 334 and the sensor element 1 in a retaining member 321 in accordance with a variation.

FIG. 9 is a side cross sectional view showing an appearance of a contact between an abutting part 334 and the sensor element 1 in a retaining member 321 in accordance with a variation. In this case, the same reference numerals as those in the retaining member 21 in accordance with the first embodiment are attached to the same constructing elements provided in the retaining member 321 as those in the retaining member 21, and a detailed description thereof will be omitted. Further, the retaining member 321 has the same crimping part 33 as the retaining member 21 in accordance with the first embodiment, although the illustration will be omitted in FIG. 9.

In the retaining member 321, the abutting part 334 is provided in a manner that a cut portion having a rectangular shape in a top elevational view in a part of the base part 30 is protruded to an opposite side to that of the retaining member 21 in accordance with the first embodiment. In other words, the abutting part 334 is the same as the abutting part 34 of the retaining member 21 in accordance with the first embodiment in that it serves as the cantilever-beam-shaped leaf spring; however, a direction in which the restoring force of the leaf spring is applied is made opposite to the case of the first embodiment.

When using the contact member 20 in which the retaining member 321 is embedded in place of the retaining member 21, each of leading end parts 334e of the abutting parts 334 which are positioned in both upper and lower sides of the sensor element 1 energizes with respect to a surface 24s in a side of the insertion port 23 of the housing member 24a. Further, since a drag at that time acts on the sensor element 1 via the base part 30 which abuts on the sensor element 1 from the vertical direction, the fixation of the sensor element 1 is achieved. In this case, the base part 30 itself comes to a contact point, and an electric continuity can be obtained with respect to the electrode terminal 1a.

Since the case mentioned above is the same as the first embodiment in that a deformation of the abutting part 334 is within the range of the elastic area, it is possible to retain and fix the sensor element 1 with a high surface pressure. Particularly, in the case that the abutting part 334 is provided in accordance with the position where the electrode terminal 1a of the sensor element 1 is provided, a great surface pressure acts at the position. Accordingly, it is possible to securely achieve the electric continuity between the base part 30 and the electrode terminal 1a. Further, there is such an advantage that it is easy to insert the sensor element 1 in the insertion port 23, in comparison with the first embodiment.

The invention claimed is:

1. A gas sensor comprising:
a sensor element; and
a contact member having an insertion port in which said sensor element is inserted and retained to obtain an electric connection with said sensor element, wherein
said contact member is provided with a plurality of sensor element retaining members having conductivity which respectively have two abutting parts abutting on said sensor element,
one of said two abutting parts is a first abutting part which is continuously bent from a base part of said sensor element retaining member towards a leading end part to form one of a linear shape and a point-like shape,
said leading end part of said first abutting part is a free end part which applies an elastic force to said sensor element while having one of point contact and line contact with said sensor element,
said sensor element retaining member and said sensor element are electrically conducted by setting said first abutting part to a contact point, and
said first abutting part of said two abutting parts is positioned in a back side of said insertion port than a second abutting part which is another of said two abutting parts.

2. A contact member having an insertion port in which a sensor element for a gas sensor is inserted and retained to obtain an electric connection with said sensor element, wherein the contact member comprises a plurality of sensor element retaining members having conductivity which respectively have two abutting parts abutting on said sensor element,
one of said two abutting parts is a first abutting part which is continuously bent from a base part of said sensor element retaining member towards a leading end part to form one of a linear shape and a point-like shape,
said leading end part of said first abutting part is a free end part which applies an elastic force to said sensor element while having one of point contact and line contact with said sensor element in a state that said sensor element is inserted and retained in said insertion port,
said first abutting part comes to a contact point which electrically conducts said sensor element retaining member and said sensor element, and
said first abutting part of said two abutting parts is positioned in a back side of said insertion port than a second abutting part which is another of said two abutting parts.

* * * * *